(12) United States Patent
Richards

(10) Patent No.: US 6,852,278 B2
(45) Date of Patent: Feb. 8, 2005

(54) APPARATUS AND METHOD FOR THE CONTROLLED RELEASE OF VOLATILE MATERIALS

(75) Inventor: Randall Richards, Canton, GA (US)

(73) Assignee: International Fragrance & Technology, Inc., Canton, GA (US)

(*) Notice: Subject to any disclaimer, the term of this patent is extended or adjusted under 35 U.S.C. 154(b) by 0 days.

(21) Appl. No.: 10/136,721

(22) Filed: Apr. 30, 2002

(65) Prior Publication Data

US 2003/0091464 A1 May 15, 2003

Related U.S. Application Data

(60) Provisional application No. 60/332,360, filed on Nov. 13, 2001.

(51) Int. Cl.[7] .................................................. A61L 9/12
(52) U.S. Cl. .............................. 422/4; 422/5; 422/123; 239/58
(58) Field of Search ........................... 422/5, 1, 123, 422/305, 120, 3, 4; 239/34, 58; 43/124, 127

(56) References Cited

U.S. PATENT DOCUMENTS 5,534,229 A 7/1996 Nomura et al.
5,672,406 A * 9/1997 Challis et al. .............. 428/136
5,974,726 A 11/1999 Creeger et al.

FOREIGN PATENT DOCUMENTS

| JP | 05285206 | | 11/1993 |
| JP | 05285206 A | * | 11/1993 |
| JP | 07178156 | | 7/1995 |
| JP | 07187267 | | 7/1995 |
| JP | 07187267 A | * | 7/1995 |
| JP | 2000070354 | | 3/2000 |
| JP | 2000070354 A | * | 3/2000 |

* cited by examiner

Primary Examiner—Elizabeth McKane
(74) Attorney, Agent, or Firm—Sonnenschen Nath & Rosenthal LLP; Brian R. McGinley

(57) ABSTRACT

A dispenser for controlling the release of volatile materials within a contained environment such as an automobile, a home, an office, a factory, or the like, comprises a housing having an opening therein, a volatile material positioned within the housing, and a temperature responsive component in operable association with the opening to regulate said opening in order to contain or release the volatile material. The temperature responsive component automatically controls the release of the volatile material in the contained environment in response to a change in the ambient temperature by uncovering or covering the opening of the housing. A method for controlling the release of volatile materials within a contained environment is also disclosed.

24 Claims, 2 Drawing Sheets

APPARATUS AND METHOD FOR THE CONTROLLED RELEASE OF VOLATILE MATERIALS

RELATED APPLICATION

Pursuant to 37 C.F.R. §1.78(a)(4) and 35 U.S.C. §119(e), this application claims the benefit of U.S. provisional application Ser. No. 60/332,360 filed Nov. 13, 2001.

BACKGROUND OF THE INVENTION

The present invention relates to the field of volatile material dispensers. In particular, the present invention is directed to a dispenser and method for controlling the release of volatile materials within a contained environment, such as an automobile, as a function of the ambient temperature within the contained environment.

Many devices have been described that deliver a fragrance, air freshener or the like within a contained environment such as a motor vehicle. One shortcoming of virtually all of such devices is their inability to automatically control the release of the fragrance from the device when the temperature within the vehicle falls or rises as a result of outside temperature changes and sunshine striking the surface of the vehicle.

This shortcoming has been partially addressed in U.S. Pat. No. 5,534,229. The '229 patent teaches the use of a liquid that contains a material that becomes hydrophobic at a specific elevated temperature. This change causes a "clogging" of the wick delivery system that significantly reduces the amount of volatile material released above a specific temperature, above about 122° F. There are several problems with the system disclosed in the '229 patent. First, the system disclosed in the '229 patent does not address the fact that reduced volatile materials are released during times of lower temperatures in the vehicle. Second, the system disclosed in the '229 patent does not account for changes in the release of volatile materials for ambient temperatures under 120° F. Finally, the system disclosed in the '229 patent requires the use of a liquid with a wick for the reduced volatilization to occur. The release of a volatile material from a solid or a gel is not affected by the inclusion of the materials that work in the liquid systems such as the system disclosed in the '229 patent.

SUMMARY OF THE INVENTION

The present invention solves the prior art problems discussed above and provides a distinct advance in the state of the art. In particular, the present invention provides a dispenser for volatile materials having a temperature responsive component that automatically controls the release of the volatile materials as a function of the ambient temperature of the surrounding environment. More particularly, the present invention is directed to a dispenser and method for controlling the release of volatile materials within a contained environment such as an automobile, a home, an office, a factory, or the like.

A first preferred embodiment of the dispenser of the present invention includes a housing having an opening therein, a volatile material positioned within the housing, and a temperature responsive component adapted to close the opening upon a change in the ambient temperature in the surrounding environment wherein flow of the volatile material through the opening is restricted. A second preferred embodiment further includes a lid in operable association with the temperature responsive component and adapted to close the opening upon a change in the ambient temperature in the surrounding environment. A method for controlling the release of a volatile material into a contained environment is also provided.

DETAILED DESCRIPTION OF THE PREFERRED EMBODIMENT

Figure 1:
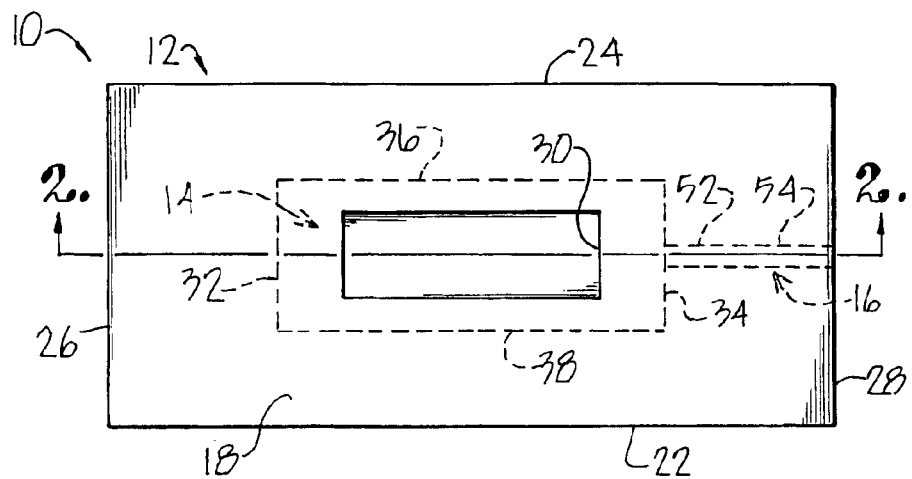
FIG. 1 is a top plan view of the dispenser of the present invention according to one preferred embodiment.
Figure 2:
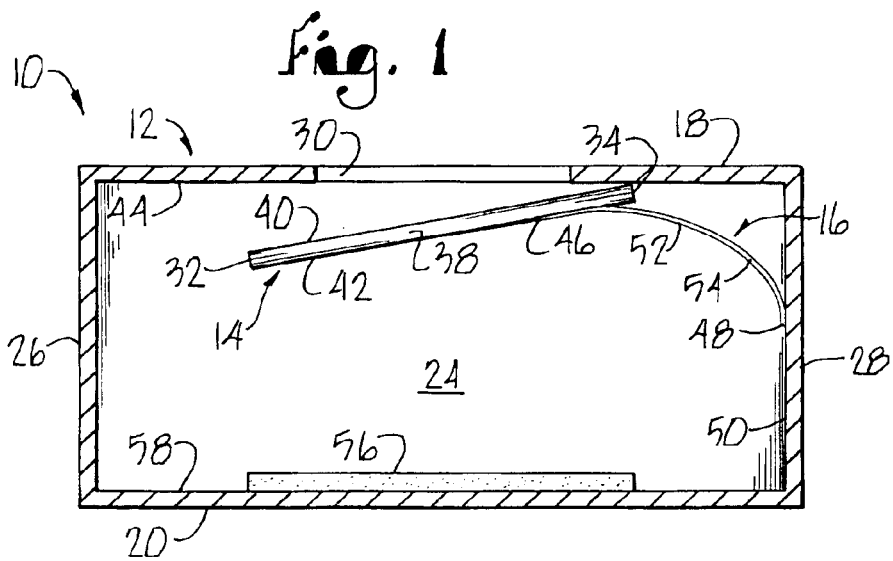
FIG. 2 is side sectional view of the dispenser of FIG. 1 taken along line A—A showing the dispenser in an open position.

The present invention is directed to a volatile material dispenser and a method for controlling the release of volatile materials, such as a clear aqueous hydrophobic gel fragrance, within a contained environment, such as an automobile, a home, an office, a factory, or the like. Referring to FIGS. 1 and 2, the dispenser 10 of the present invention comprises a housing 12, a lid 14 and a temperature responsive component 16. The preferred housing 12 is generally rectangular so that it may be positioned on a horizontal or vertical planar surface, but it will be appreciated that other shapes would be equally functional. Housing 12 comprises a top wall 18, bottom wall 20, front wall 22, back wall 24, first side wall 26 and second side wall 28. In the preferred embodiment, bottom wall 20 is generally flat in order to stabilize housing 12 on a planar surface and to maintain housing 12 in an upright position. Housing 12 may be constructed from any material that is compatible with the desired volatile material to be dispensed therefrom including, but not limited to, plastics, metals, composites, epoxies, wood, stone, ceramic, and glass. The preferred material for the construction of housing 12 is plastic including polyvinyl chloride, polyethylene terephthalate, polyethylene, polypropylene, polystyrene, polycarbonate, ABS and polymethylpentene. The most preferred materials are polyethylene terephthalate and polymethylpentene.

Top wall 18 defines a generally rectangular opening 30 therein configured to be closed by lid 14. Generally rectangular lid 14 presents dimensions larger than that of opening 30 but smaller than that of top wall 18. Lid 14 is relatively flat and comprises a first end 32, second end 34, third end 36, fourth end 38, top face 40 and bottom face 42. Lid 14 is laterally positioned within housing 12 beneath top wall 18 and opening 30 so that top face 40 cooperatively engages the inner face 44 of top wall 18 and covers substantially all of opening 30.

Figure 3:
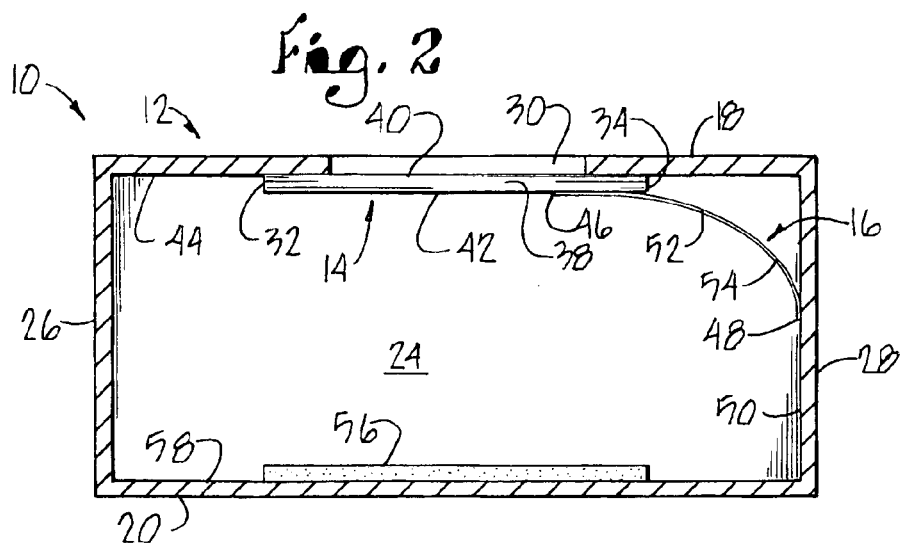
FIG. 3 is side sectional view of the dispenser of FIG. 1 taken along line A—A showing the dispenser in a closed position.

Temperature responsive component 16 comprises a front end 46 and a back end 48. Front end 46 is coupled with bottom face 42 adjacent second end 34 of lid 14 and back end 48 is coupled with the inner face 50 of side wall 28. Temperature responsive component 14 may be formed of any material that expands and deforms when the ambient temperature surrounding dispenser 10 changes. The preferred component 14, as shown in FIGS. 1—3, comprises a bimetal composite having a first metal 52 and a second metal 54 coupled together wherein first metal 52 has a different coefficient of expansion than second metal 54 such that, at a desired temperature, first metal 52 will expand causing component 14 to deform and raise toward top wall 18.

Finally, a volatile material 56 is positioned on the inner face 58 of bottom wall 20. It will be appreciated that volatile material 56 may be positioned anywhere within housing 12 depending upon the shape and size of housing 12 in any particular application. Volatile material 56 may be any material that will significantly volatilize at an ambient temperature of interest including, but not limited to, the following materials: fragrances, perfumes, odorants, organic solvents, insecticides, insect repellants or attractants, pesticides, herbicides, odor counteractants and disinfectants.

The normal state of dispenser 10 is shown in FIG. 2 wherein lid 14 is in an open position. First metal 52 and second metal 54 are in their unexpanded state and lid 14 therefore does not restrict opening 30. Fragrance from volatile material 56 flows freely through opening 30 to freshen the air outside of dispenser 10. As the ambient temperature surrounding dispenser 10 increases, first metal 52 and second metal 54 slowly expand at different rates causing component 16 to deform and raise lid 14 toward inner face 44 of top wall 18. The deformation of component 16 continues until lid 14 cooperatively engages the inner face 44 of top wall 18 thereby closing off opening 30 to prevent flow of volatile material 56 through opening 30. Dispenser 10 in this closed position is shown in FIG. 3. The amount of volatile material 56 that is released through opening 30 can be further regulated by the size of housing 12, the size of opening 30, the size of lid 14 and the expansion characteristics of the materials used to construct temperature responsive component 16 which, upon expansion and deformation, controls the position of lid 14. Additional openings (not shown) may also be provided to allow for a constant low level release of volatile material 56 from dispenser 10 even when lid 14 is in a closed position. Thus, the release of volatile material 56 through opening 30 is controlled by the position of lid 14 which is used to cover or restrict opening 30 to varying degrees as a function of the effect of the ambient temperature on component 16. The embodiment discussed above is ideal wherein volatile material 56 is an automobile air freshener or a perfume and it is desirable to restrict the flow of volatile material 56 from dispenser 10 as the temperature increases. It will be appreciated that it is also within the scope of the present invention to construct temperature responsive component 16 from materials that expand as the ambient temperature decreases rather than increases. This can be useful if, for instance, an insect repellant is to be released, and as the temperature increases more repellant is needed because the insects are more active. The degree of restriction needed, the temperatures at which component 16 expands, the size of opening 30 and the type and size of lid 14 will therefore be dictated by the conditions of use of dispenser 10 and type of volatile material 56 being positioned therein. Other embodiments of construction and materials are contemplated for temperature responsive component 16 by the present invention. For example, component 16 could be formed from two different plastics of differing expansion coefficients. Component 16 could also be a bladder containing a gas solubilized in a liquid that would expand upon a change in temperature and push against lid 14 to close opening 30. If the gas had variable solubility at changing temperatures it could be used as a deformation component. Alternatively, the dispenser 10 could be configured such that component 16 itself causes the restriction of opening 30 and serves as the closing mechanism to prevent flow of volatile material 56. It is also contemplated by the present invention to position lid 14 and component 16 outside of housing 12.

Figure 4:
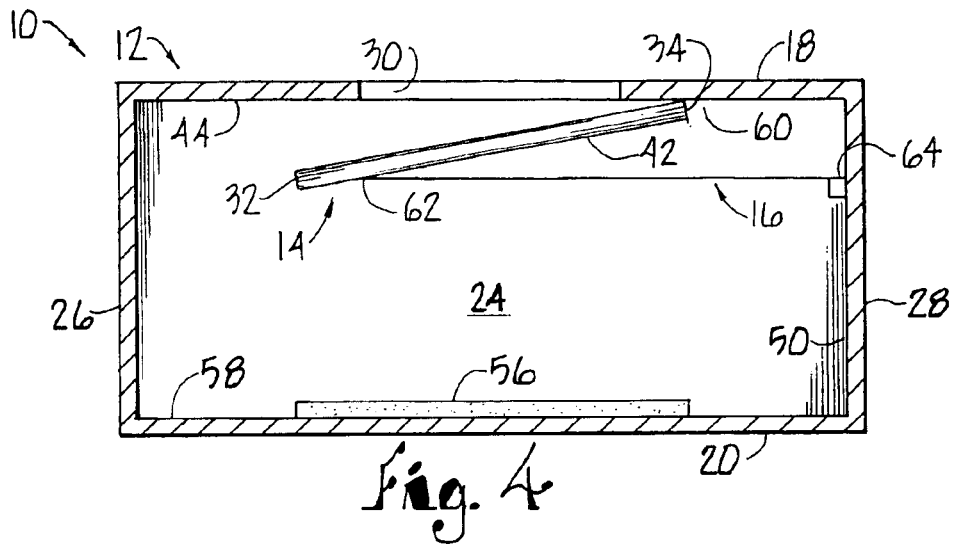
FIG. 4 is a side sectional view of the dispenser of the present invention in a second preferred embodiment.

FIG. 4 shows another preferred embodiment of the present invention wherein second end 34 of lid 14 is hingedly attached to inner face 44 of top wall 18 by hinge 60. Temperature responsive component 16 comprises a lever having a front end 62 and a back end 64 wherein back end 64 is attached to inner face of 50 of side wall 28 and component 16 projects toward lid 14 so that front end 62 engages the bottom face 42 of lid 14. As component 16 expands in response to a change in ambient temperature, front end 62 deforms and raises toward top wall 18. As component 16 raises, it pushes lid 14 toward opening 30 until lid 14 cooperatively engages the inner face 44 of top wall 18 thereby closing off opening 30 resulting in a restriction on the flow of volatile material 56 from dispenser 10 to the outside environment. In an alternative embodiment, dispenser 10 may be configured without lid 14 such that temperature responsive component 16 itself cooperatively engages the inner face 44 of top wall 18 to close opening 30 and restrict the flow of volatile material 56 through opening 30.

Figure 5:
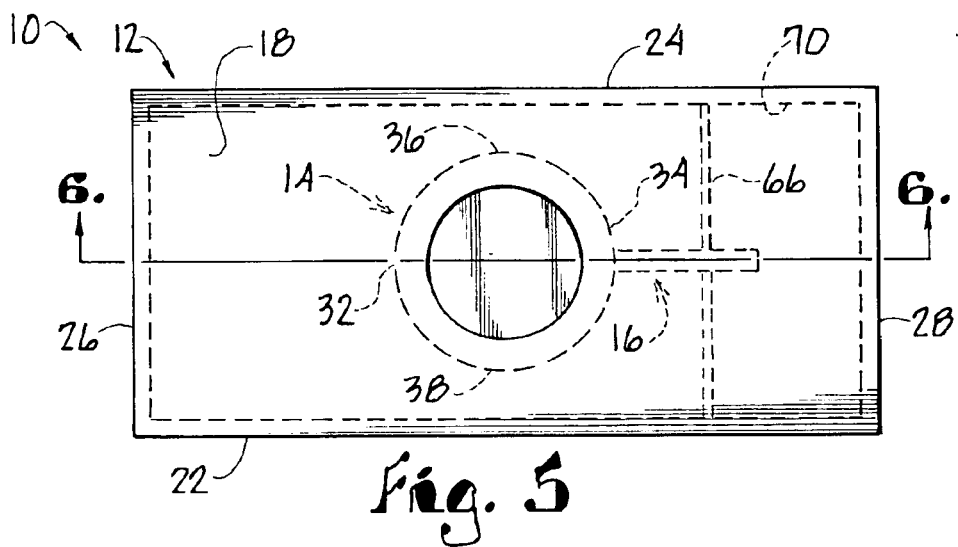
FIG. 5 is a top plan view of the dispenser of the present invention in a third preferred embodiment.
Figure 6:
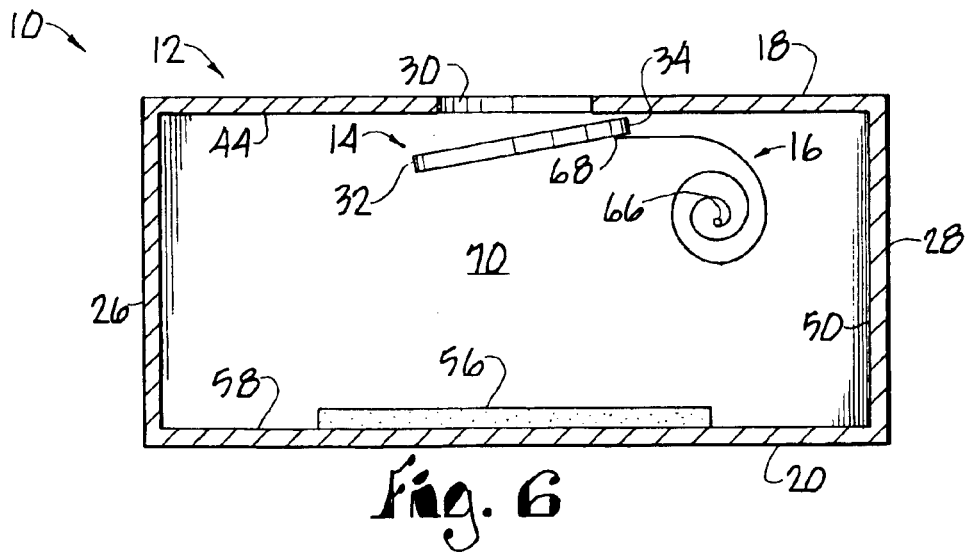
FIG. 6 is a side sectional view of the dispenser of FIG. 6 taken along line B—B showing the dispenser in an open position.

Another preferred embodiment of the present invention is shown in FIGS. 5 and 6 wherein temperature responsive component 16 is a spring having a first end 66 and a second end 68. First end 66 is attached to a shaft projecting from the inner face 70 of back wall 24 and second end is coupled to second end 34 of lid 14 as shown in its open position in FIG. 5. Opening 30 and lid 14 are generally circular with lid 14 presenting a circumference greater than that of opening 30 but less than the dimensions of top wall 18. As the ambient temperature surrounding dispenser 10 changes, component 16 expands and raises lid 14 until lid 14 engages inner face 44 thereby closing opening 30 as shown in FIG. 6.

The dispenser of the present invention may be used in any environment where the ambient temperature changes significantly and where there is a need to control the release of a volatile material in response to that changing temperature. One particularly preferred environment is the interior of a motor vehicle. Rapid fragrance loss at elevated temperatures occurs with virtually all prior automobile air fresheners. The present invention is especially well-suited to this environment due to the widely fluctuating temperatures that a vehicle interior can experience. In the summer the temperature can easily reach 160° F. in the direct sunshine. In winter below-freezing conditions can be found in many parts of the world. Dispenser 10 can restrict the release of volatile material 56 at high temperatures in the summer and promote the release of volatile material 56 in the winter. Private personal vehicles, such an automobile or small truck, as well as public transportation can benefit from the dispenser 10 of the present invention which can control the release of volatile material 56. Dispenser 10 can also be integrated into the air conditioning and heating systems of vehicles with the same benefits resulting from a controlled release of volatile material 56.

Although it is believed to be apparent from the foregoing discussion, the present invention also comprises a method of controlling the release of a volatile material within a contained environment. The method comprises providing a housing having an opening therein and a temperature responsive component adapted to close the opening by expanding upon a change in the ambient temperature of the surrounding environment, positioning a volatile material within the housing and changing the ambient temperature of the surrounding environment.

It should be recognized that there are many options regarding how and where to place the various interfaces and the variations should not limit the spirit or intent of the present invention. It should be further recognized that any of the known technologies utilized for apparatus and methods for the controlled release of volatile materials and the like may be incorporated within the present invention.

The foregoing description of the embodiments of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and modifications as are suited to the particular use contemplated. It is intended that the scope of the invention not be limited by the specification, but be defined by the claims set forth below.

What is claimed is:

1. A dispenser for use in a contained environment comprising:
   (a) a housing having at least one opening therein;
   (b) a solid or gel volatile material positioned within the housing;
   (c) a temperature responsive component positioned adjacent said opening; and
   (d) wherein said temperature responsive component comprises first and second movable members, said first member having a different thermal coefficient of expansion than said second member such that said temperature responsive component moves to restrict or enlarge said opening based on an increase or decrease in the ambient temperature of said contained environment.

2. The dispenser of claim 1 wherein said housing is made of a material selected from the group consisting of plastics, metals, composites, epoxies, wood, stone, ceramic, and glass.

3. The dispenser of claim 1 wherein said plastics are selected from the group consisting of polyvinyl chloride, polyethylene terephthalate, polyethylene, polypropylene, polystyrene, polycarbonate, ABS and polymethylpentene.

4. The dispenser of claim 1 wherein said volatile material is selected from a group consisting of fragrance, perfume, insect repellants, insect attractants, pesticides, herbicides, odorants, odor counteractants, organic solvents and disinfectants.

5. The dispenser of claim 1 wherein said temperature responsive component is made of a material that expands upon a change in ambient temperature of said contained environment.

6. The dispenser of claim 1 wherein said temperature responsive component comprises a first and second metal wherein said first metal wherein said first metal has a different coefficient of expansion that said second metal.

7. The dispenser of claim 1 wherein said first and second member comprises a first and second plastic wherein said first plastic has a different coefficient of expansion than said second plastic.

8. The dispenser of claim 7, said temperature responsive component comprising a lever wherein said lever operably engages said lid to close said opening.

9. The dispenser of claim 7, said temperature responsive component comprising a spring wherein said spring operably engages said lid to close said opening.

10. The dispenser of claim 1, said dispenser further comprising a lid in operable association with said temperature responsive component and adapted to close said opening.

11. A dispenser for use in a contained environment comprising:
   (a) a housing having at least one opening therein;
   (b) a solid or gel volatile material positioned within said housing;
   (c) a lid adapted to close said opening; and
   (d) a temperature responsive component in operable association with said lid, said component being adapted to operably engage said lid upon a change in the ambient temperature of said contained environment to close said opening thereby restricting flow of said volatile material through said opening; and
   (e) wherein said temperature responsive component comprises first and second movable members, said first member having a different thermal coefficient of expansion than said second member such that said temperature responsive component moves to restrict or enlarge said opening based on an increase or decrease in the ambient temperature of said contained environment.

12. The dispenser of claim 11, wherein said housing is made of a material selected from the group consisting of plastics, metals, composites, epoxies, wood, stone, ceramic, and glass.

13. The dispenser of claim 12, said plastics being selected from the group consisting of polyvinyl chloride, polyethylene terephthalate, polyethylene, polypropylene, polystyrene, polycarbonate, ABS and polymetnylpentene.

14. The dispenser of claim 11 wherein said volatile material is selected from a group consisting of fragrance, perfume, insect repellants, insect attractants, pesticides, herbicides, odorants, odor counteractants, organic solvents and disinfectants.

15. The dispenser of claim 11, wherein said temperature responsive component is made of a first and second metal wherein said first metal has a different coefficient of expansion than said second metal.

16. The dispenser of claim 11, wherein said temperature responsive component is formed of a first and second plastic wherein said first plastic has a different coefficient of expansion than said second plastic.

17. The dispenser of claim 11, said temperature responsive component comprises a lever.

18. The dispenser of claim 11, said temperature responsive component comprises a spring.

19. A method for controlling release of a solid or gel volatile material into a contained environment comprising the steps of:
   (a) providing a housing having an opening therein and a temperature responsive component adapted to close said opening by expanding upon a change in the ambient temperature of said contained environment, wherein said temperature responsive component comprises first and second movable members, said first member having a different thermal coefficient of expansion than said second member such that said temperature responsive component moves to restrict or enlarge said opening based on an increase or decrease in the ambient temperature of said contained environment;
   (b) positioning a volatile material within said housing; and
   (c) selectively dispensing the volatile material into the contained environment based upon and increase or decreasing in the ambient temperature of said contained environment.

20. The method of claim 19 wherein said temperature responsive component is made of a material selected from the group consisting of plastics, metals, composites, epoxies, wood, stone, ceramic, and glass.

21. The method of claim 20, said plastics being selected from the group consisting of polyvinyl chloride, polyethylene terephthalate, polyethylene, polypropylene, polystyrene, polycarbonate, ABS and polymethylpentene.

22. The method of claim 19 wherein said volatile material is selected from a group consisting of fragrance, perfume, insect repellants, insect attractants, pesticides, herbicides, odorants, odor counteractants, organic solvents and disinfectants.

23. The method of claim 19 wherein said temperature responsive component comprises a first and second metal wherein said first metal has a different coefficient of expansion than said second metal.

24. The method of claim 19 wherein said temperature responsive component comprises a first and second plastic wherein said first plastic has a different coefficient of expansion than said second plastic.

* * * * *